United States Patent [19]

Vanlerberghe et al.

[11] 4,297,102

[45] Oct. 27, 1981

[54] CYCLICAL TENSIO-ACTIVE POLYETHERS

[75] Inventors: Guy Vanlerberghe, Claye-Souilly; Henry Sebag, Paris, both of France

[73] Assignee: L'Oreal, Paris, France

[21] Appl. No.: 20,656

[22] Filed: Mar. 15, 1979

[30] Foreign Application Priority Data

Mar. 17, 1978 [FR] France .................. 78 07914

[51] Int. Cl.$^3$ .......................... C07D 323/00
[52] U.S. Cl. ............................ 8/406; 8/415; 8/435; 424/70; 260/338; 544/86; 546/187
[58] Field of Search .............. 260/338; 544/148, 86; 546/207, 187; 424/70; 8/406, 415, 435

[56] References Cited

U.S. PATENT DOCUMENTS 4,138,427 2/1979 Vanlerberghe et al. .......... 260/459

OTHER PUBLICATIONS

Chemical Abstracts, vol. 86, 171908g & 5082cs.

Primary Examiner—Paul M. Coughlan, Jr.
Attorney, Agent, or Firm—Fleit & Jacobson

[57] ABSTRACT

Cyclical polyethers having amphiphile groups are derived from the tetramer of epichlorhydrin. These are useful in the solubilization of various products.

28 Claims, No Drawings

CYCLICAL TENSIO-ACTIVE POLYETHERS

The invention has as its goal new cyclical tensio-active polyethers, the procedures for operating them and mixtures containing them.

The new cyclical tensio-active polyethers have remarkable properties which differentiate them from similar compounds described up to the present. By their chemical structure, they resemble crown ethers, which have been studied extensively in the course of recent years as complexing agents of cations of alkaline or alkaline earth metals.

They are differentiated by their amphiphile characteristic, i.e. an affinity for water and for organic media, which gives them a strong interfacial activity.

They are also distinguished from conventional surface agents which include a single lipophile chain per molecule.

As is well known, the latter, when dissolved in water, show a set of properties—beyond a threshold of concentration termed "critical micellar concentration" (CMC)—which have a large number of applications. In particular, for concentrations at least equal to the CMC, they dissolve in water organic substances such as liposoluble dyes and hydrocarbons.

The compounds according to the invention possess dissolving properties at infinitely small concentrations, quite lower than the CMC of the surface agents which include a lipophile chain of comparable length.

This is an important advantage for certain uses of tensio-actives such as, for examople, in pharmaceutical or cosmetic mixtures or compositions where it is advantageous to reduce as much as possible the amount of tensio-active compound used in order not to interfere with the active principle of these mixtures.

Besides, the compounds of the invention are harmless and less irritative for the skin or mucous membranes, in particular the mucous membranes of the eyes, than surface agents including a single lipophile chain per molecule and comparable functional groups.

The new cyclical tensio-active polyethers may be represented by the general formula

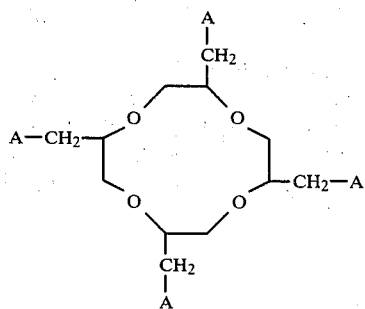

in which A refers to an amphiphile ensemble composed of a hydrophile part and of a lipophile part, this amphiphile ensemble being linked to the ring by the hydrophile part; the hydrophile part is composed of one or several elements selected from the group comprising amino, amino oxide, ammonium, ammonio alkanoate, ammonio alkyl sulphonate, ammonio alkyl sulphinate, thioether, sulphoxide, sulphonium, sulphoxonium, ether, hydroxyl, esther, amide, and acid functions; the lipophile part is composed of one or several groupings selected from the group comprising: aliphatic groupings having from 1 to 20 carbon atoms, (ii) substituted aliphatic groupings having from 7 to 20 carbon atoms, (iii) alkylaryl groupings having from 7 to 20 carbon atoms, the alkyl part of the alkylaryl grouping having up to 14 carbon atoms.

Among the unsubstituted aliphatic groupings, the substituted aliphatic groupings and the alkylaryl groups present in the amphiphile ensemble A, one may cite as an example the alkyl, hydroxyalkyl, alkenyl, alkylphenyl, benzyl and alkylbenzyl groupings.

The general formula (I) may also be written in the simplified form:

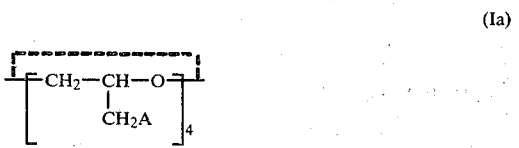

As amphiphile grouping A, one may cite, for the sake of example, the following:

(a) the grouping

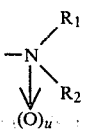

where

R$_1$ and R$_2$, identical or different, refer to aliphatic radicals and preferably alkyl, hydroxyalkyl or alkenyl having from 1 to 20 carbon atoms, with one of the radicals including at least 8 carbon atoms; or substituted aliphatic radicals having from 6 to 20 carbon atoms or alkylaryl radicals having from 6 to 20 carbon atoms; the sum of the carbon atoms of R$_1$ and R$_2$ being, preferably, less than or equal to 28; one of the radicals may, also, refer to a dimethylamino-ethyl or; propyl radical, diethylamino; and ethyl or; propyl radical, piperidino; ethyl or; propyl radical, morpholino-ethyl or; propyl radical or alkyl polyhydroxy propylene radical;

u refers to zero or 1;

(a$_1$) the grouping

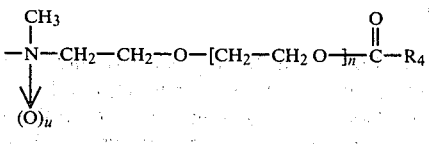

where

R$_4$ refers to a non-substituted or substituted aliphatic radical or an alkylaryl radical having from 6 to 20, in particular from 8 to 16 and more particularly from 12 to 16 atoms of carbon and is preferably an alkyl, hydroxyalkyl, alkenyl or alkylphenyl radical, the alkyl part of the alkylphenyl radical having up to 14 carbon atoms;

n refers to a whole number or a fraction from 1 to 20, preferably from 1 to 10, in particular from 2 to 8 and more particularly from 4 to 6;

u refers to the number 0 or 1;

(a$_2$) the grouping

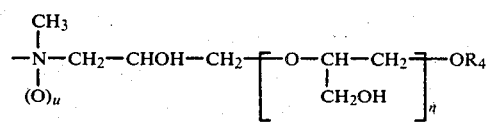

u, $R_4$ and n having the meaning shown above.

(b) the grouping

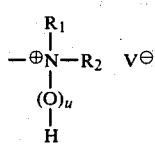

($b_1$) the grouping

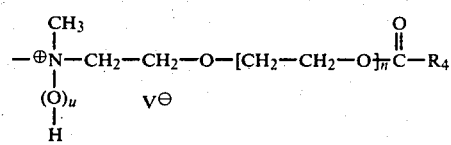

($b_2$) the grouping

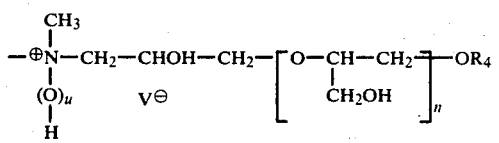

where
  u refers to the number 0 or 1
  n refers to a whole number or a fraction from 1 to 20, preferably from 1 to 10, in particular from 2 to 8 and more particularly from 4 to 6;
  $V^\ominus$ refers to an anion and preferably a formiate, acetate, citrate or lactate anion, $R_1$, $R_2$, $R_4$ have the meanings mentioned earlier.

(c) the grouping

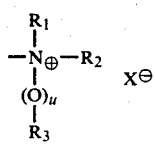

$R_1$, $R_2$ and u having the same meaning as above,
$R_3$ refers to an alkyl radical or hydroxylalkyl radical having from 1 to 3 carbon atoms and preferably a methyl, ethyl, hydroxyethyl, dihydroxypropyl radical; or a benzyl radical;
$X^-$ refers to an anion and preferably a chloride, bromide, iodide, monomethyl sulphate, methyl sulphonate, p.toluene sulphonate;

($c_1$) the grouping

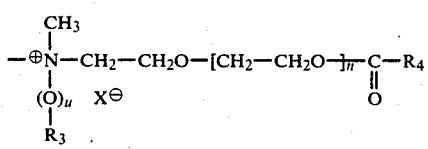

($c_2$) the grouping

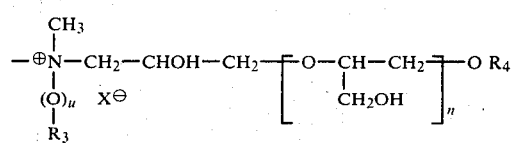

in these groupings ($c_1$) and ($c_2$)
  u refers to the number 0 and 1
  n refers to a whole number or a fraction from 1 to 20, preferably from 1 to 10, in particular from 2 to 8 and more particularly from 4 to 6;
  $R_4$ has the meanings mentioned above.

(d) the grouping

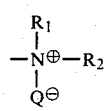

where $Q^\ominus$ refers to one of the following groupings:

$-(CH_2)_m-COO^\ominus$ where m refers to 1, 2, or 3

$-CH_2-CH_2-CH_2-SO_3^\ominus$ $-CH_2-CH_2OSO_2^\ominus$ ($d_1$) the grouping

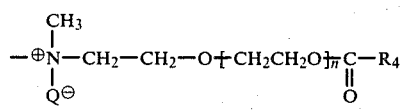

($d_2$) the grouping

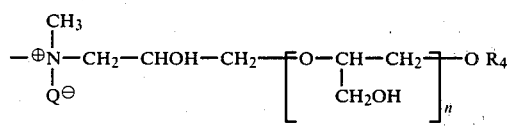

in the groupings ($d_1$) and ($d_2$)
  n refers to a whole number or a fraction from 1 to 20, preferably from 1 to 10, in particular from 2 to 8 and more particularly from 4 to 6;
  $Q^\ominus$ has the meaning shown for the grouping (d).

(e) the grouping

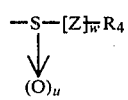

where
  $R_4$ refers to a non-substituted or substituted aliphatic radical or an alkylaryl radical having from 6 to 20, in particular from 8 to 16 and more particularly from 12 to 16 carbon atoms and preferably an alkyl, hydroxyalkyl, alkenyl, alkylphenyl radical, with the alkyl part of the alkyl phenyl radical having up to 14 carbon atoms,
  u refers to zero or 1;
  w refers to zero or 1;

Z refers to atom groupings with hydrophile characteristics which may be ether, ester, amide, amine, ammonium and/or hydroxyl.

As an example of groupings Z, we may cite the following:

$$-CH_2-CHOH-$$

$$-(CH_2-CH_2O)_n-$$

$$-(CH_2-CH_2O)_n-\overset{O}{\underset{\parallel}{C}}-$$

$$-(CH_2)_x-COO-$$

$$-(CH_2)_2-COOCH_2-CHOH-$$

$$-(CH_2)_x-CONH-$$

$$-(CH_2)_x-\underset{\underset{N}{\overset{|}{(CH_2)_y}}}{CON-}\diagdown\overset{CH_3}{\underset{CH_3}{\diagup}}$$

where
 x represents 1 or 2;
 y represents 2 or 3;
 n represents some number from 1 to 20.
 (e₁) the grouping $$-\underset{(O)_u}{\overset{\downarrow}{S}}-CH_2-CH\diagup^{O-[CH_2-CH_2-O]_j-\overset{\parallel}{\underset{O}{C}}-R_4}_{CH_2-O-[CH_2-CH_2-O]_k-\overset{\parallel}{\underset{O}{C}}-R_4}$$

j and k, identical or different, refer, each one, to a whole number or a fraction lower than 20, the sum j+k being included between 1 and 20.

(f) the grouping $$Y-\left[-CH_2-CH-CH_2-O-\right]_p-L$$
$$\phantom{Y-\left[-CH_2-\right.}\underset{L}{\overset{|}{O}}\phantom{-CH_2-O-\left.\right]_p-L}$$
$$\phantom{Y-\left[-CH_2-\right.}\underset{L}{|}\phantom{-CH_2-O-\left.\right]_p-L}$$

where
 L refers at the same time to a hydrogen atom and to one of the groupings $$-CH_2-CHOH-CH_2-(O)_q-R_5$$

where q refers to 0 or 1

$$-\overset{\parallel}{\underset{O}{C}}-\overset{|}{\underset{SO_3H}{CH}}-R_5$$

$$-\overset{\parallel}{\underset{O}{C}}-CH_2-R_5$$

the hydrogen atom and the other grouping being distributed in statistical fashion;
$R_5$ refers to a linear alkyl radical having from 6 to 18 and in particular from 8 to 16 carbon atoms;

p refers to a whole number or a fraction from 1 to 10, in particular from 2 to 8, more particularly from 3 to 6, and represents an average statistical value;
Y refers to: —O—; —S— or $$-\underset{O}{\overset{\downarrow}{S}}-$$

(g) the grouping $$-O-[CH_2-CH_2-O]_v-\overset{\parallel}{\underset{O}{C}}-\overset{|}{\underset{R_6}{CH}}-R_5$$

where
 v refers to a whole number or a fraction from 0 to 20, in particular from 0 to 10, more particularly from 0 to 5;
 $R_6$ refers to a hydrogen atom or the radical —SO₃H;
 $R_5$ having the meaning indicated above;

(h) the grouping (e) and (e₁) alkylated by an alkylation agent chosen from the group formed by bromide, iodide and dimethyl sulphate and preferaby by dimethyl sulphate;

(i) the grouping (f) alkylated by an alkylation agent chosen from the group formed by bromide, iodide and dimethyl sulphate and preferably by dimethyl sulphate;

The tensio-active cyclical polyethers of type Ia corresponding to formula (I) in which A refers to the grouping (a)

$$-\underset{(O)_u}{\overset{\downarrow}{N}}\diagdown^{R_1}_{R_2}$$

are not soluble in water in this form, but they may lead to soluble products by salification or alkylation.

The tensio-active cyclical polyethers of formula (I) in which A refers to one of the groupings (a₁), (a₂), (b), (b₁), (b₂), (c), (c₁), (c₂), (d), (d₁), (d₂), (e), (e₁), (f), (g), (h), (i) are generally soluble in water.

The tensio-active cyclical polyethers according to the invention are all obtained from polychlorinated cyclical polyethers, tetramer of epichlorhydrine, of the formula:

(III)

$$Cl-CH_2-\underset{\underset{Cl}{CH_2}}{\overset{\overset{CH_2}{|}}{\underset{O}{\overset{Cl}{|}}}}\cdots-CH_2-Cl$$

This formula may be written in simplified form:

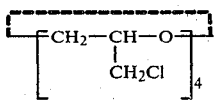
(IIIa)

The tetramer of epichlorohydrine is prepared in a well known manner by polymerization of epichlorohydrine in the presence of a Lewis acid catalyst, such as $BF_3$, $SnCl_4$ or $SbCl_5$ and purified by fractionation under reduced pressure. The preparation of this compound is described in example I.

The tetramer of epichlorohydrine of formula (III) reacts with the secondary amines between 80° and 150° C. and preferably between 130° and 150° C., at the normal pressure or in autoclave, in the possible presence of a solvent chosen among the lower alcohols, $C_1$–$C_4$, the alkoxyethanols, the diethers of glycol, dimethylformamide or methyl caprolactam, giving tensio-active cyclical polyethers of the type I(a) (compounds of formula (I) in which A refers to the grouping (a)

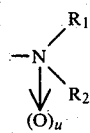
(a)

where $R_1$, $R_2$ and u have the meanings indicated above.

The compounds of the type I($a_1$), corresponding to the formula I in which A refers to the grouping ($a_1$)

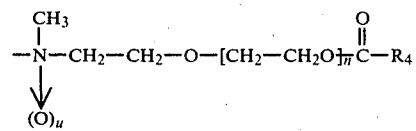
($a_1$)

where u, n, $R_4$ have the meanings indicated above, may be prepared by having methylethanolamine react with the tetramer of epichlorhydrine of formula (III); one then fixes n moles of ethylene oxide on the product obtained earlier and one esterifies the functions OH with an acid of formula $R_4$—COOH where $R_4$ has the meaning indicated above.

The compounds of type I($a_2$) corresponding to the formula I in which A refers to the grouping ($a_2$)

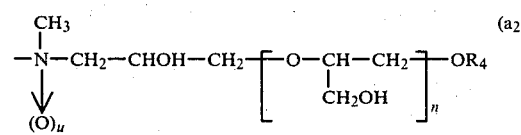
($a_2$)

where u, $R_4$ and n have the meaning indicated above, may be prepared by having the tetramer of epichlorhydrine of formula III react with a large excess of methylamine. On the product thereby obtained one condenses a compound of the formula:

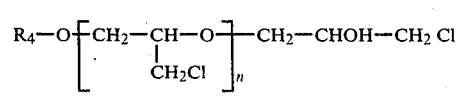

(which one may be prepared by polyaddition of n+1 moles of epichlorhydrine on one mole of compound of formula $R_4OH$, $R_4$ having the meaning indicated above).

One finally replaces, in the intermediary compound thereby obtained, the chlorine atoms by hydroxyl groups with the help of sodium or potassium acetate, followed by hydrolysis or alcoholysis of the acetic ester formed.

This preparation procedure is described in more detail in French Pat. No. 1,538,525, which corresponds to U.S. Pat. Nos. 3,879,464 and 4,009,255.

The compounds of type I(b), I($b_1$) and I($b_2$) corresponding to formula I in which A refers to the grouping (b), ($b_1$) or ($b_2$)

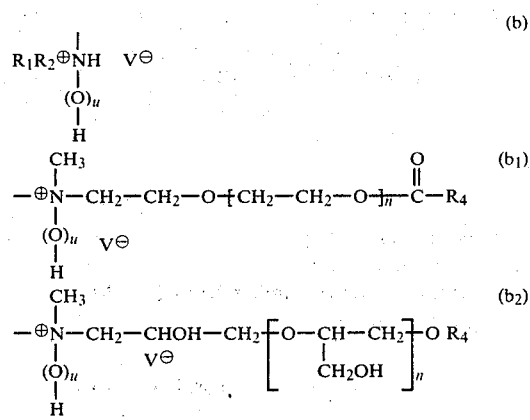

where $R_4$, $V^-$, u, n have the meanings indicated above, may be prepared respectively by salification of the groupings (a), ($a_1$) or ($a_2$)

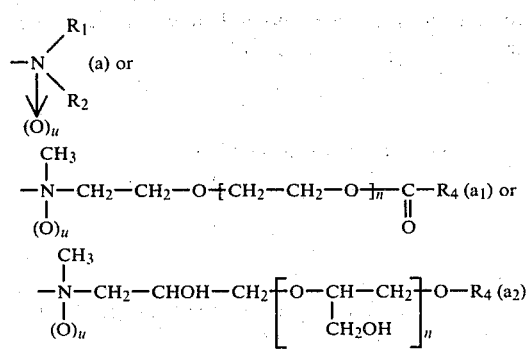

of a compound of the type I(a), I($a_1$), I($a_2$) with an appropriate acid, preferably with an organic acid, chosen preferably among the formic, acetic, citric, lactic, tartric acids.

The compounds of the type I(c), I($c_1$) and I($c_2$) corresponding to the formula (I) in which A refers respectively to the grouping (c), ($c_1$) or ($c_2$)

(c)

-continued $$-\overset{\oplus}{\underset{\underset{R_3}{\overset{|}{(O)_u}}}{N}}-CH_2-CH_2O-[CH_2-CH_2-O]_{\overline{n}}-\underset{\overset{\|}{O}}{C}-R_4 \quad (c_1)$$
$$X^{\ominus}$$

$$-\overset{\oplus}{\underset{\underset{R_3}{\overset{|}{(O)_u}}}{N}}-CH_2-CHOH-CH_2\left[O-\underset{\underset{CH_2OH}{|}}{CH}-CH_2\right]_n O\ R_4 \quad (c_2)$$
$$X^{\ominus}$$

may be prepared respectively by alkylation of the grouping (a), (a$_1$) or (a$_2$) of a compound of the type I(a), I(a$_1$) or I(a$_2$).

One uses, preferably, an alkylating agent of formula X R$_3$, where X and R$_3$ have the meanings indicated above.

Among these alkylating agents one may mentioned chloride, bromide, iodide of methyl, dimethyl or diethyl sulphate, methane sulphonate of methyl, p.toluene sulphonate of methyl, monochlorhydride of glycol and of glycerol. Dimethyl sulphate is more particularly preferred.

The compounds of type I(c) may still be obtained by reaction of the tetramer of epichlorhydrine of formula (III) with the short chain secondary amines, of the formula:

$$HN\begin{matrix}R_1'\\ \\R_2'\end{matrix}$$

where R'$_1$ and R'$_2$ refer to an alkyl or hydroxyalkyl having from 1 to 3 carbon atoms, followed by an alkylation with a mesylate or tosylate of an alcohol or a mixture of alcohols having from 8 to 20 carbon atoms.

The compounds of the type I(c$_2$) may also be prepared by reaction of the tetramer of epichlorhydrine of formula (III) with compounds of the formula:

$$R-O-(CH_2-\underset{\underset{CH_2Cl}{|}}{CH}-O)_n-CH_2-CHOH-CH_2-N\begin{matrix}R_1'\\ \\CH_3\end{matrix}$$

where R, R'$_1$ and n have the meanings indicated above, followed by hydrolysis of the chloro-methylated groupings.

Among the short chain secondary amines, one may mention for the sake of example dimethylamine and methylethanolamine.

Compounds of the type I(d), I(d$_1$), I(d$_2$) corresponding to the formula (I) in which A refers respectively to the grouping (d), (d$_1$), or (d$_2$)

$$-\overset{+}{\underset{\underset{CH_3}{\overset{|}{Q^-}}}{N}}-R_2 \quad (d)$$
$$R_1$$

$$-\overset{\oplus}{\underset{Q^{\ominus}}{N}}-CH_2-CH_2-O-[CH_2\ CH_2\ O]_{\overline{n}}-\underset{\overset{\|}{O}}{C}-R_4 \quad (d_1)$$
$$CH_3$$

$$-\overset{\oplus}{\underset{Q^{\ominus}}{N}}-CH_2-CHOH-CH_2\left[O-\underset{\underset{CH_2OH}{|}}{CH}-CH_2\right]_n OR_4 \quad (d_2)$$
$$CH_3$$

where R$_1$, R$_2$, Q$^{\ominus}$, n, have the meanings indicated above, may be obtained by alkylation respectively of a compound of the type I(a), I(a$_1$), I(a$_2$) with one of the following reagents:

the acids of the formulas $$Cl(CH_2)_m-COOH$$

$$Br(CH_2)_m-COOH$$

where m refers to 1, 2 or 3

$$ClCH_2-CH_2-CH_2-SO_3H$$

$$BrCH_2-CH_2-CH_2-SO_3H,$$

sodium or potassium salt of such an acid, sultone propane of the formula:

$$\begin{matrix}CH_2-CH_2-CH_2\\ |\qquad\qquad\qquad|\\ O\text{\textemdash}\text{\textemdash}\text{\textemdash}SO_2\end{matrix}$$

or glycol sulphite of the formula:

$$CH_2OH-CH_2-OSO_2H.$$

The compounds of the type I(e) corresponding to the formula (I) in which A refers to the grouping $$\underset{\underset{(O)_u}{\Downarrow}}{-S}-[Z]_w-R_4 \quad (e)$$

R$_4$, u, w, having the meaning indicated above and Z refers to $$-CH_2-CHOH-$$

or $$-(CH_2-CH_2O)_n-$$

where n refers to a whole number or a fraction from 1 to 20 may be obtained by reaction of the tetramer of epichlorhydrine of formula (III) with alkyl mercaptans, hydroxyalkyl mercaptans, alkyl mono- or poly-ethoxy mercaptans, the alkyl and hydroxyalkyl groupings having from 6 to 20 carbon atoms.

The compounds of type I(e) in the formula of which z refers to $$-\!\!\!\!+\!\!CH_2-CH_2-O\!\!+\!\!\!_{\overline{n}}\overset{\|}{\underset{O}{C}}-$$

may be prepared by a procedure in three stages:

(1) Condensation of thioethanol with the tetramer of epichlorhydrine of formula (III).

(2) Addition of 1 to 20 moles of ethylene oxide on the compound obtained in the first stage.

(3) Esterification of the compound obtained in the second stage by an acid of formula $R_4COOH$.

To prepare the compounds of the type (e) in which Z refers to

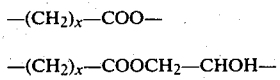

—$(CH_2)_x$—COO—

—$(CH_2)_x$—COOCH$_2$—CHOH—

—$(CH_2)_x$—CONH—

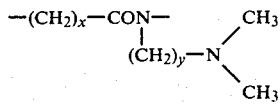

where x refers to 1 or 2 and y refers to 2 or 3, one proceeds in two stages.

In a first stage, one causes the tetramer of epichlorhydrine of formula (III) to react with a methylic or ethylic ester of a mercaptoacetic or mercapto propionic acid of the formula:

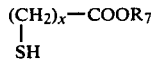

where x refers to 1 or 2 and $R_7$ refers to $CH_3$ or $C_2H_5$;

The reactions of condensation of the mercaptans and of the esters of a mercapto acetic or mercapto propionic acid with the tetramer of epichlorhydrine of formula (III) are carried out in the presence of a basic compound, for example an alkaline alcoholate such as methylate or ethylate of sodium or potassium, preferably in solvents, at a temperature between 80° and 150° C.

The usable solvents are the alkanols having from 1 to 4 carbon atoms or the alkoxyethanols such as methoxy-, ethoxy-, butoxy-ethanol, possibly in the presence of a small quantity of water, when one uses alkyl, hydroxyalkyl or alkyl mono- or poly-ethoxy mercaptans.

In a second stage one transforms the intermediary compound of formula (IV) below, obtained in the first stage.

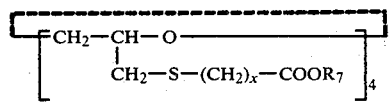

where x and $R_7$ have the meanings indicated above, into compounds of the type I(e) defined above.

By causing the intermediary compound of formula (IV) to react with an alcohol of formula $R_4OH$ where $R_4$ refers to an alkyl, hydroxyalkyl or alkenyl radical having from 6 to 20 carbon atoms, one obtains the compound of formula (V);

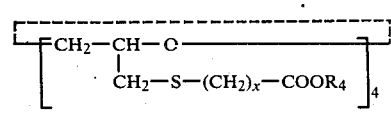

$R_4$ having the meaning indicated above.

By reaction of the intermediary compound of formula (IV A)

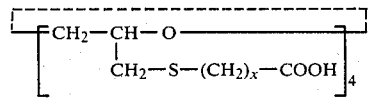

(obtained by saponification or hydrolysis of the compound of formula (IV)) with the epoxy-1,2 alkanes of the formula:

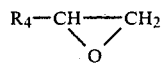

one obtains the compounds of formula (VI)

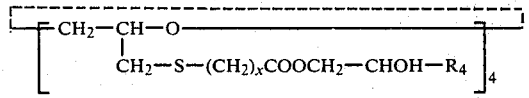

These reactions are carried out in the presence of alkaline catalysts such as methylate or ethylate of sodium or of potassium, at a temperature between 60° C. and 140° C.

By causing the intermediary compound of formula (IV) to react on a primary amine of formula $R_4 NH_2$, $R_4$ having the meaning above, one obtains, after elimination of methanol or of ethanol the compound of the formula:

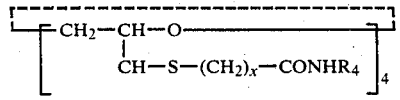

By causing the intermediary compound of formula (IV) to react with a secondary amine of the formula:

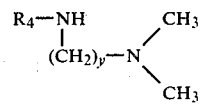

where $R_4$ and y have the meanings indicated above one obtains the tensio-active compound of the formula:

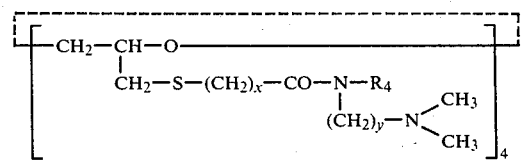

The reactions of the intermediary compound of formula (IV) with a primary or secondary amine occur generally at a temperature between 20° and 120° C. in the presence, possibly, of methylate of sodium or potassium.

In a general fashion the compounds of the type I(e) responding to the formula (I) in which A refers to the grouping

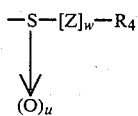

$R_4$, u and w have the meanings indicated above.

Z refers to the groupings of atoms with hydrophile characteristics under the form of a radical including one or several groupings of ether, ester, amide, amine, ammonium and/or hydroxyle, which may be prepared from the basis of the tetramer of epichlorhydrine of formula (III) in one, two, three or four stages.

The compounds of type I(e) with thioether grouping thus prepared may possibly be oxidated into sulphoxides with hydrogen peroxid of 30-35% w/v, in a stoechiometric quantity, at a temperature of 20°-50° C. and preferably from 30°-35° C., in the presence of 0.1 to 10% of carboxylic acid having from 1 to 4 carbon atoms and preferably in the presence of acetic acid and possibly in the presence of a customary solvent.

The compounds of thioether and sulphoxide grouping may be transformed, respectively, into sulphonium and sulphoxonium compounds by alkylation with an alkylating agent of the classical type and preferably with bromide or iodide of methyl or dimethyl sulphate.

The tertiary amine groupings of the compounds of type I(e) may be transformed into quaternary ammonium groupings by alkylation with a classical alkylating agent and preferably with bromides or iodides of methyl or dimethyl sulphate.

The tensio-active cyclical polyethers of type $I(e_1)$ responding to the formula:

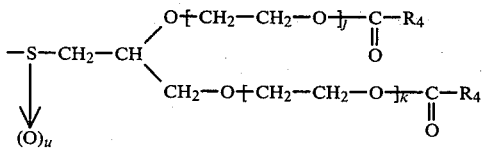

where
j and k refer, each one, to a whole number or to a fraction lower than 20 and the sum j+k is included between 1 and 20;
$R_4$ has the meaning indicated above
may be prepared by condensation of thioglycerol with the tetramer of epichlorhydrine of formula (III) followed at first by an oxyethylenation of the derivative obtained and then by esterification with an acid of formula $R_4COOH$.

The compounds thus obtained may be oxidized and/or alkylated as the compounds of type I(e).

The compounds of type I(f) corresponding to the formula (I) in which A refers to the grouping:

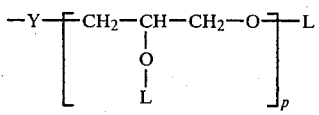

where Y, I and p have the meanings indicated above, may be prepared in two different ways according to the meaning of Y.

When Y refers to an oxygen atom, the compounds of the type I(f) may be prepared by reaction, in alkaline catalysis, of the hydroxylated derivative of the tetramer of epichlorhydrine (compound of formula II above) with glycidol, the intermediary compound obtained reacting with an oxide of alkylene of the formula:

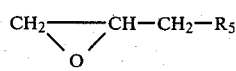

or with an alkyl glycidylether of the formula:

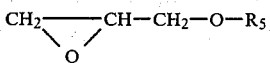

When Y refers to a sulphur atom or a sulphoxide grouping, the compounds of type I(f) may be prepared by a procedure in three stages.

In a first stage one prepares an intermediary compound of the formula:

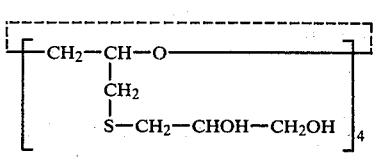

(IX)

at a temperature of 80°-150° C., by reaction of the tetramer of epichlorhydrine of formula (III) with thioglycerol, in the presence of a solvent chosen among the lower alkanols having from 1 to 4 carbon atoms and in the presence of an alkaline compound preferably chosen among the alkaline hydroxides such as sodium or potassium hydroxide and the alkaline alcoholates, for example methylate or ethylate of sodium or of potassium.

In a second stage one causes to react on this intermediary compound (IX) 0 to 9 moles of glycidol and/or of oxides of alkylene having from 8 to 20 carbon atoms and/or alkyl glycidyl ether (such as those mentioned above), at a temperature of 120°-170° C. and preferably around 150° C., in the presence of an alkaline compound of the same type as that used in the first stage, this compound obtained in the second stage possibly being able to be esterified with a sulfocarboxylic acid having from 8 to 20 carbon atoms.

One uses, preferably, glycidol which reacts essentially with the primary alcohol grouping of the intermediary compound of formula (IX). A small fraction of glycidol may react with the secondary alcohol grouping.

When in the second stage one causes r moles of glycidol to react (r refers to a whole number or decimal from 0 to 9), one obtains a tensio-active compound represented essentially by the formula:

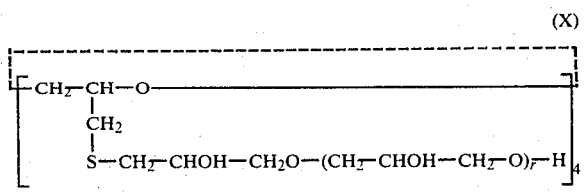
(X)

It is possible to make react, in a third stage, on this compound (X) s moles (s refers to a whole number or decimal from 1 to 9) of an oxide of alkylene and/or of an alkyl glycidyl ether and/or of a sulfocarboxylic acid and/or of a carboxylic acid having from 8 to 20 carbon atoms.

By reaction of an oxide of alkylene on the intermediary compound of formula (X) one obtains the compound of the type I(f) in which I refers to $$-CH_2-CHOH-CH_2-R_5.$$

By reaction of an alkylglycidylether on the compound of formula (X) one obtains the compound of type I(f) in which L signifies $$-CH_2-CHOH-CH_2-O-R_5.$$

The hydroxyl functions may be esterified by a carboxylic acid of formula $R_5-CH_2-COOH$ or by an α-sulphocarboxylic acid of the formula

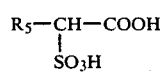

where $R_5$ has the meaning indicated above.

The compounds of type I(f) of thioether grouping may possibly be oxydized into sulphoxides with hydrogen peroxid.

The compounds of type I(f) as well as their sulphoxides may also be alkylated and transformed respectively into sulphonium or sulphoxonium compounds.

Oxydation and alkylation are carried out as for the compounds of type I(e).

By hydrolysis of the polychlorinated cyclical polyether, tetramer of epichlorhydrine of formula (III) one obtains the compound of formula (II)

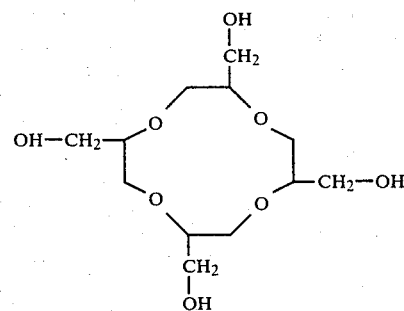
(II)

This formula may be written in simplified form as follows:

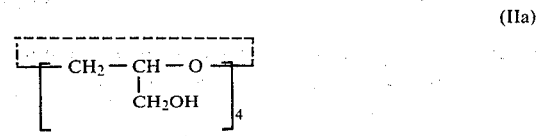
(IIa)

One carries out the hydrolysis of the polychlorinated cyclical polyether of formula (III) by replacing the chlorine atoms by a —OH grouping, by reaction with an alkaline salt of carboxylic acid and preferably with acetate of sodium or of potassium at a temperature of 100° to 190° C. in an appropriate solvent chosen preferably among the glycols and the derivatives of glycol and preferably among ethyleneglycol, butyleneglycol, diethyleneglycol and its ethers, propyleneglycol, dipropyleneglycol, hexyleneglycol and 2-butoxyethanol; the acetic ester formed is then decomposed by saponification by means of sodium or potassium hydroxide or by alcoholysis by means of a lower alcohol and preferably by means of methanol or ethanol in the presence of a basic catalyst chosen preferably among methylate or ethylate of sodium or of potassium.

By reaction of v moles of ethylene oxide on the hydroxylated derivative of the tetramer of epichlorhydrine of formula (II) one obtains an intermediary compound of the formula:

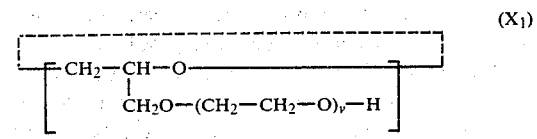
(X₁)

whose hydroxyl functions may be esterified either with a sulphocarboxylic acid of the formula

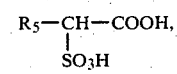

or with a carboxylic acid of formula $R_5-CH_2-COOH$, where $R_5$ refers to a linear alkyl radical having from 6 to 18 carbon atoms.

One thus obtains a compound of type I(g) corresponding to the formula (I) in which A refers to the grouping:

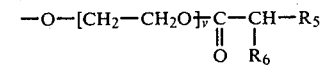

where $R_6$ refers either to $SO_3H$ or to H, v refers to a whole number or a fraction equal to or less than 20, with the exception of the number zero.

One may also cause to react on the compound of formula (II) directly either a sulphocarboxylic acid of the formula:

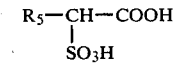

where $R_5$ refers to a linear alkyl radical having from 6 to 18 carbon atoms. One thus obtains a compound of type I(g) in which $R_6$ refers to $SO_3H$ and v refers to the number 0.

This reaction is carried out at a temperature from 100° C. to 120° C. and one eliminates the water formed.

The tensio-active cyclical polyethers of formula (I) according to the invention are present in the form of thick oil, of paste or of wax generally soluble or dispersible in water.

They reduce the surface tension of the water and permit, at very low concentrations, the solubilization of non-hydrosoluble products.

Among the non-hydrosoluble compounds which may be solubilized by the tensio-active cyclical polyethers of formula (I) must be cited dyes, perfumes, and certain pharmaceutical products.

Other than the solubilization of these products, the cyclical tensio-active compounds of formula (I) may permit the solubilization or the dispersion of mineral or polar compounds in an organic medium or of hydrophobe compounds in an aqueous medium.

The compounds of these invention may be used in industry, especially in cosmetic compositions, pharmaceuticals, in textile industries, paint and insecticide industries and in similar industries.

The invention has also as a goal the compositions including at least one tensio-active cyclical polyether of formula (I).

Among these compositions it is necessary to mention more particularly the cosmetic or pharmaceutical compositions including at least $0,5.10^{-2}$ grams per liter or $0,5.10^{-3}\%$ in weight of tensio-active cyclical polyether of formula (I).

The cosmetic compositions include especially compositions designed for the care of the skin, nails, and hair.

The compositions for the care of the hair concern especially shampoos and conditioning mixtures for the hair, as well as dyeing or coloring compositions.

The cosmetic compositions may be in the form of an aqueous hydroalcoholic solution, or in the form of a creme, a gel, an emulsion or an aerosol.

The hydroalcoholic solutions include generally an alcohol having from 1 to 4 carbon atoms and preferably ethanol or isopropanol, preferably in a proportion of 5 to 70% of the total weight of the composition.

The invention also has as an aim a cosmetic composition for the treatment of hair, especially a shampoo, containing in solution in a solvent chosen from a group formed by water and a hydroalcoholic solution, a cosmetically effective amount of one or several tensio-active cyclical polyethers of formula (I).

The cosmetic compositions for the treatment of the hair and in particular shampoos may also contain in addition to a tensio-active cyclical polyether of formula (I), also an adjuvant chosen from the group formed by the anionic, cationic, amphotere, zwitterionic or non-ionic tensio-actives, perfumes, dyes, preservatives, foam synergists, foaming agents, foaming stabilizers, softening agents, strengthening agents for the hair, anti-dandruff agents, cosmetic resines and electrolytes.

The invention also relates to a dye composition for keratinous fibers, especially for human hair, and more particularly to a dye composition containing in an aqueous or aqueous alcoholic solution at least one cyclical tensio-active polyether of formula (I) as well as one or several dyes selected from the group of direct dyes and more particularly from the group consisting of anthraquinone dyes, azoic dyes, nitrobenzene dyes, indoanilines, indophenols and indamines. Generally said dyes are present in amounts of about 0.001 to 1% by weight of said composition.

The dye composition can also contain various adjuvants usually employed in cosmetics for the hair and more particularly adjuvants selected from the group consisting of anionic, cationic, non-ionic, amphoteric tensio-active or surface active agents, perfumes, preservatives, thickeners, softeners, electrolytes, sequestring agents, penetrating agents, swelling agents and cosmetic resines.

The pH of the cosmetic compositions including shampoos, coloring shampoos and dye compositions is from 3 to 11.

The invention also relates to a process for treating and/or conditioning the hair which comprises applying to living human hair on effective amount of an aqueous or hydroalcoholic composition including one or several tensio-active cyclical polyethers of formula (I) and possibly one or several adjuvants defined above.

The invention will be better understood with the aid of non-limiting examples of the type:

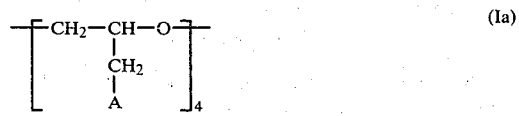

(Ia)

EXAMPLE 1

Preparation of the cyclical tensio-active compound of type I(a) of the formula:

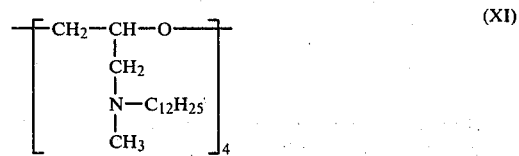

(XI)

In a first stage one prepares the tetramer of epichlorhydrine of formula (III)

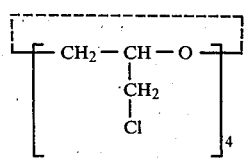

In a reactor of 6 liters, one mixes: 1180 g of epichlorhydrine and 500 ml of carbon tetrachloride.

One chills the mixture to 10° C. by immersion in an ice bath.

Under heavy agitation, one adds, in 6 hours, 16 g of etherate of $BF_3$ (trifluoride of boron) in solution in 1 liter of carbon tetrachloride.

One keeps throughout this period the temperature between 10° and 13° C.

One then lets the temperature rise and the mixture is carried, progressively, to reflux during 1 hour.

One adds 50 g of dry sodium carbonate, finely pulverized. The mixture is agitated 2 hours at reflux. The mineral salts are separated by filtration. The carbon tetrachloride is evaporated under reduced pressure, then one fractionates by distillation.

One thus gathers, at 185° C., under 0.2 mm of Hg, 210 g of the product which is present in the form of an uncolored vitreous mass cristallizing at the end of several days.

Dose of organic chlorine: 10.6 meq/g.

In a second stage one prepares the cyclical tensio-active compound of formula (XI).

One heats in a nitrogen atmosphere, at a temperature of 140° C., for 12 hours:
  14.8 g (0.04 mole) of the compound III and
  64.8 g (0.32 mole) of N-methyl laurylamine.

After return to the laboratory temperature, one adds, under agitation, 150 ml of pentane. The chlorhydrate of methyl laurylamine is dried, then washed two times with 50 ml of pentane.

The filtrate is concentrated, first under ordinary pressure, then under 30 mm of Hg while raising the temperature of the bath up to 90° C.

One obtains 43.5 g of product which one dries by heating for 6 hours in the oven at 105° C.

Index of basicity: 3.84 meq/g Theory: 3.90 meq/g.

The tensio-active compound thus obtained is perfectly soluble in water in the presence of lactic acid.

EXAMPLE 2

Preparation of the cyclical tensio-active compound of the type I(c) of the formula:

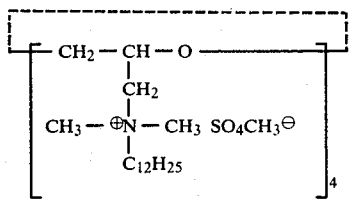

(XII)

One dissolves 15 g of basic compound (0.051 mole) of example 1 in 20 g of pure methanol.

Under agitation one adds 6.2 g (0.048 mole) of sulphate of dimethyl in 35 minutes. The temperature rises to 43° C. The mixture is agitated for 4 hours at 45° C. The solvent is eliminated by distillation under reduced pressure at 40° C.

One obtains a clear brown paste, soluble in hot water, soluble in cold in a hydroethanolic solution containing 50% of ethanol.

EXAMPLE 3

Preparation of the cyclical tensio-active compound of type I(a) of the formula:

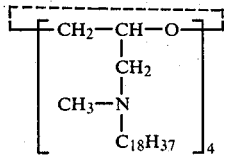

(XIII)

One dissolves 9.25 g (0.025 mole) of tetramer of epichlorhydrine of formula (III) and 28.3 g (0.1 mole) of N-methyl stearylamine, in 30 g of dimethylether of diethyleneglycol.

The mixture is heated at 135° C. for 30 hours and the acid is neutralized as it appears with methylate of sodium (0.090 meq/g). Sodium chloride is separated by filtration in heat. The solvent is eliminated by distillation under reduced pressure.

One obtains a brown solid, soluble in water in the presence of lactic acid, and having the following characteristics:
  Index of basicity: 2.63–2.64 meq/g
  Theory: 2.93 meq/g
  Dosage of chlorine: 0
  Drop point: 33° C.

EXAMPLE 4

Preparation of cyclical tensio-active compound of type.I(c) of the formula:

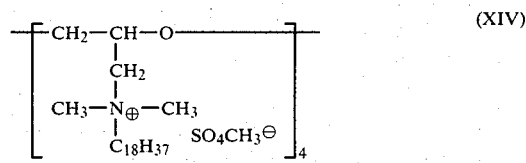

(XIV)

One adds 10 g of methanol to 7.9 g (0.020 mole) of tetramer of epichlorhydrine previously melted.

At a temperature of 30° C., one adds, under great agitation, 2.5 g (0.020 mole) of dimethyl sulphate in solution in 5 g of methanol. The length of the addition is 5 minutes, the temperature rises to 45° C. The mixture is agitated for 2 hours at 45° C.

The methanol is eliminated by distillation under a pressure of 40 mm of Hg.

One obtains 10.4 g of tensio-active product of the formula above which is present in the form of a hard paste of brown color, soluble in water.

EXAMPLE 5

Preparation of the cyclical tensio-active compound of type I(a) of the formula:

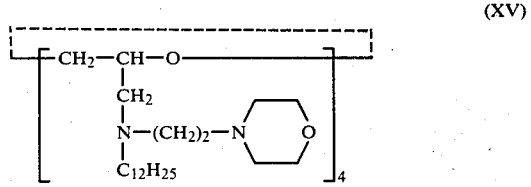

(XV)

To 7.4 g (0.02 mole) of tetramer of epichlorhydrine, melted, one adds 25 g (0.08 mole) of N-morpholino-ethyl laurylamine. The mixture is heated for 35 hours at 135° C.

Every three hours an acid index is done, and the acid formed is neutralized with a corresponding amount of sodium methylate. One then adds 20 ml of benzene. The sodium chloride is separated by filtration and washed with two times 5 ml of benzene. The solvent is eliminated by distillation under reduced pressure.

One obtains a tensio-active product which is soluble in water in the presence of lactic acid.

EXAMPLE 6

Preparation of tensio-active cyclical polyether of type I(c), obtained by quaternization of the compound of example 5 with dimethyl sulphate.

To 6.4 g (36 meq in basicity) of compound (XV) prepared in example 5, one adds, at 20° C., 2.26 g (18 meq) of dimethyl sulphate.

After 2 hours of agitation, one obtains a thick brown oil soluble in water.

EXAMPLE 7

Preparation of cyclical tensio-active compound of type I(i) of the formula:

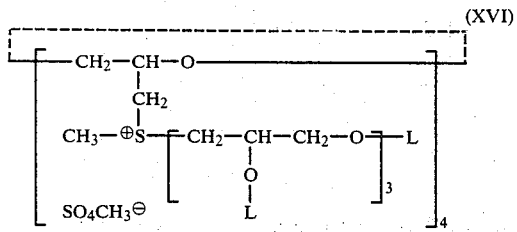

L refers to hydrogen and the grouping

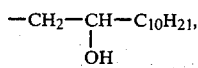

distributed in statistical fashion in the proportions 3/1.

(a) In a first stage one prepares an intermediary compound of the formula:

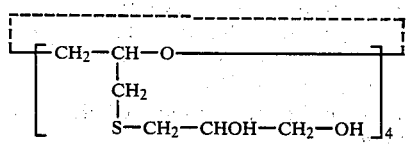

One dissolves, in 50 g of absolute ethanol:
18.5 g (0.05 mole) of tetramer of epichlorhydrine
24.2 g (0.2 mole) of thioglycerol
32 g of methanolic liquor of sodium methylate at 6.3 meq/g.

The mixture is carried to reflux for 24 hours. Sodium chloride is separated by filtration and washed with 30 ml of absolute ethanol.

After elimination of the solvent by heating under reduced pressure, one obtains the desired compound whose hydroxyl index is 11.2 meq/g and whose sulphur content is 19%.

(b) In a second stage one adds to 14 g (170 meq of hydroxyl grouping) of intermediary compound prepared in the first stage, 0.42 g of sodium methylate in methanol (containing 5 meq/g of sodium methylate), then at a temperature of 150° C., 12.5 g of glycidol (170 meq) in the space of an hour.

(c) In a third stage, to 5.65 g (0.005 mole) of intermediary compound prepared in the second stage, one adds 0.2 g of sodium methylate, then at the temperature of 150° C., 3.7 g of epoxy-1,2 dodecane (0.02 mole) in solution in 7 ml of solution of isopropanol at 85%, distilling all the while the isopropanol and the water.

The reactional mixture is heated for 7 hours at 150° C.

(d) In a fourth stage, one prepares the cyclical tensio-active compound of formula (XVI).

One dissolves, in 7 ml of methanol, 6.8 g of product prepared formerly then one adds, at 45° C., in 10 minutes, 1.83 g of dimethyl sulphate solubilized in 7 ml of methanol.

After 30 minutes of heating at reflux, the methanol is eliminated by distillation under reduced pressure.

The product thus obtained is present in the form of a brown paste, soluble in water with a light opalescence.

EXAMPLE 8

Preparation of cyclical tensio-active compound of the type I(f) of the formula

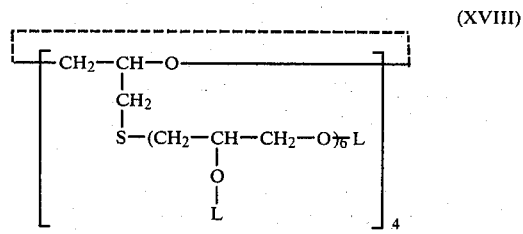

L refers to hydrogen and the grouping $-CH_2-CHOH-C_{10}H_{21}$ in the proportions 6/1 distributed in statistical fashion.

To 8.3 g of intermediary compound of formula (XVII) prepared in example 7), containing 100 meq (milliequivalent) in hydroxyl grouping, one adds 2.2 g of sodium methylate at 4.6 meq/g, then at 150° C., in the space of 1 hour 20 minutes, 19 g of glycidol (250 meq).

Heating is maintained for 20 minutes after the end of addition.

One then adds 9.2 g (50 meq) of epoxy-1,2 dodecane at the temperature of 150° C. in the space of 1 hour 20 minutes. Heating is thus maintained during 6 hours.

The product obtained is present in the form of a brown paste soluble in water.

EXAMPLE 9

Procedure for preparation of a cyclical tensio-active compound of the type I(c) of the formula:

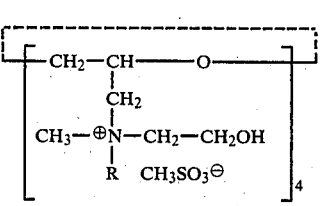

R=mixture of $C_{12}-C_{15}$ alkyl radicals derived from "Dobanol 25" alcohols sold by SHELL.

Dobanol 25 includes primary alcohols having 12 to 15 carbon atoms, in the following approximate proportions in weight:

| | |
|---|---|
| Alcohol in $C_{12}$ | 20% |
| $C_{13}$ | 33% |
| $C_{14}$ | 29% |
| $C_{15}$ | 18% |

(a) To 7.4 g (0.02 mole) of tetramer of epichlorhydrine, one adds 16 g of methyl ethanolamine (0.2 mole), then one heats the mixture at 135° C. for 20 hours. One neutralizes the acid formed with 15 g of sodium methylate to 5 meq/g in the presence of 25 ml of benzene. Sodium chloride is separated by filtration.

After elimination of the solvent by heating under reduced pressure, one obtains a brown oil whose index of basicity is 7.17 meq/g.

(b) To 4.9 g (35.2 meq in amine) of derivative thus obtained, one adds 2 g of absolute ethanol, then in 15 minutes, 11 g of sulphonic methane ester of a mixture of primary alcohols in $C_{12}$–$C_{15}$ sold under the trademark "Dobanol 25" dissolved in 5.5 g of absolute ethanol.

One heats, at 45° C. during 10 hours, then again 10 hours at 90° C. After elimination of the ethanol, one obtains a brown paste soluble in water.

EXAMPLE 10

Preparation of the cyclical tensio-active compound of the type I(g) of the formula:

$$\left[ -CH_2-CH-O- \atop \begin{array}{c} | \\ CH_2 \\ | \\ O \\ | \\ CO \\ | \\ CH-SO_3H \\ | \\ R_5 \end{array} \right]_4 \quad (XX)$$

where $R_5$ refers to the alkyl radical $C_{14}H_{29}$.

In a first stage one prepares the hydroxylated intermediary compound of the formula:

$$\left[ -CH_2-CH-O- \atop \begin{array}{c} | \\ CH_2 \\ | \\ OH \end{array} \right]_4 \quad (IIA)$$

by "hydroxylation" (replacement of the halogene atom by a hydroxyl group) of the tetramer of epichlorhydrine by means of acetate of potassium and alcoholysis of the acetic ester formed.

Under a nitrogen atmosphere, one mixes:

7.4 g (0.02 mole) of tetramer of epichlorhydrine of formula (III)

7.85 g (0.08 mole) of pure dry potassium acetate 10 g of glycol dipropylene.

The mixture is heated to 145° C. for 5 hours under agitation. The potassium chloride is dried, then washed two times with 10 ml of absolute ethanol.

The solvents are eliminated by distillation under a pressure of 1 mm of Hg, carrying the temperature up to 130° C. The weight obtained is 7.5 g. The product is put in solution in 10 ml of absolute ethanol. One adds 0.1 g of methylate of sodium at 6.2 meq/g. One leaves it for 24 hours at the surrounding temperature.

The solution is neutralized with an ethanolic solution of chlorhydric acid.

The ethanol is eliminated by distillation under a pressure of 40 mm of Hg.

The product is desolvated by heating in the oven at 105° C. for 8 hours.

One obtains the intermediary compound of formula (IIA) having a hydroxyl index of 13.5–14.05 meq/g. (Theory: 13.5 meq/g).

(b) In a second stage one dissolves 1 g of compound (IIA) and 4.6 g of sulphopalmitic acid in 18 g of water. One heats it to 100° C. and one distills the water at ordinary pressure then under reduced pressure.

One takes up the reactional mass with 40 g of toluene which one adds progressively to bring along the water formed in the course of the reaction. One thus obtains a paste of brown-black color, soluble in water.

EXAMPLE 11

Preparation of a mixture of cyclical tensio-active compounds of the type $I(a_1)$ of the formula:

$$\left[ -CH_2-CH-O- \atop \begin{array}{c} | \\ CH_2 \end{array} \right]_4$$
$$CH_3-N-CH_2-CH_2O-(CH_2-CH_2O)_n-\underset{\underset{O}{\|}}{C}-R_4$$

in which n represents an average statistical value of 5.8 and $R_4$ refers to the radical $C_{11}H_{23}$.

(a) To 20 g of compound prepared according to the example 9a, one adds 1.2 g of methanolic solution of sodium methylate at 5.85 meq/g.

The methanol is eliminated under reduced pressure.

One heats it to a temperature of 180° C. and passes under agitation a current of oxide of ethylene for 14 hours. The increase in weight corresponds to a statistical condensation of 5.8 moles of oxide of ethylene by OH grouping.

The product is dissolved in 100 ml of isopropanol and the catalyst neutralized with chlorhydric acid in isopropanolic solution. After filtration the solvent is eliminated under reduced pressure.

One obtains a brown oil, soluble in water, whose index of basicity is 2.16 meq/g and the index of hydroxyls: 2.8 meq/g.

(b) 10.7 g of product thus obtained (30 meq in OH grouping) are mixed with 6.45 g of methyl laurate (0.03 mole).

After addition of 0.26 g of sodium methylate at 5.8 meq/g, one heats the reactional mass for 3 hours at 100° C. under agitation.

One thus obtains a brown oil, soluble in water.

One may, by the addition of a mineral or organic acid, prepare the corresponding salts of formula $b_1$.

EXAMPLE 12

Preparation of a cyclical tensio-active compound of type I(a) of the formula:

$$\left[ -CH_2-CH-O- \atop \begin{array}{c} | \\ CH_2 \\ | \\ N{\nearrow}^{CH_3}_{\searrow C_{12}H_{25}} \\ \downarrow \\ O \end{array} \right]_4$$

7.2 g of compound prepared according to example I (28 meq in amine groupings) are dissolved in 7 g of isopropanol, then the mixture is heated under agitation at 60° C.

One then adds in 1 hour 5.7 ml of hydrogen peroxid at 130 volumes (39% in weight). After 17 hours at 60° C., the reaction rate is practically quantitative. After concentration under reduced pressure, one obtains a clear yellow paste, dispersible in water and soluble in the presence of acid.

Index of basicity: 3.7 meq/g.

EXAMPLE 13

Preparation of a cyclical tensio-active compound of type I(e) of the formula:

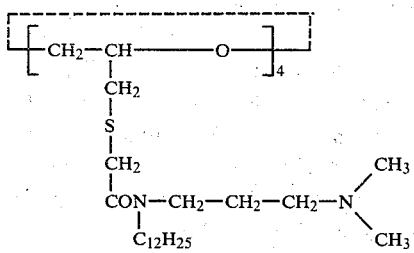

One adds, under nitrogen, to 9.25 g of tetramer of epichlorhydrine prepared according to example I (100 meq in chlorine) dissolved in 60 g of absolute ethanol, 12 g of thioglycolate of ethyl (0.1 mole).

One then heats the reactional mass to 60° C. and one adds 17.1 g of sodium methylate at 5.86 meq/g.

After 16 hours of heating, the reactional mass is diluted with 30 ml of ethyl acetate and the sodium chloride is eliminated by filtration.

The solvent is evaporated under reduced pressure.

One thus obtains a yellow oil whose index of saponification is 6.5 meq/g. to 8.7 g of compound thus obtained, one adds 13.7 g of N-dodecyl, N', N'-dimethyl propylene diamine-1,3 and 0.42 g of sodium methylate at 5.8 meq/g.

The reactional mass is heated to 130° C. for 45 hours.

One thus obtains a thick oil, deep brown, soluble in an acid medium.

EXAMPLE 14

Preparation of a mixture of cyclical tensio-active compounds, of type I(c₂) of the formula:

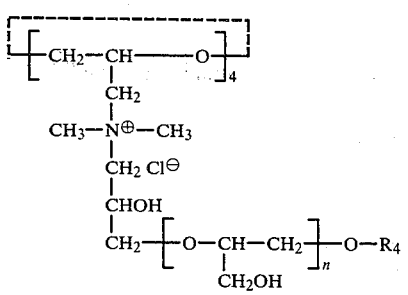

in which n refers to an average statistical value of 3 and $R_4$ refers to $C_{12}H_{25}$.

To 39.5 g of polychlorinated compounds prepared by polyaddition of 4 moles of epichlorhydrine to 1 mole of dodecanol-1, in the presence of trifluoride of boron (temperature of 50° C.), one adds 40 g of dimethylamine pure, and 100 ml of absolute ethanol.

The reactional mixture is heated in an autoclave at 80° C. for 4 hours. The product is then taken up with 100 ml of acetate of ethyl and washed with water; after drying of the organic phase on sodium sulphate, one eliminated the solvent under reduced pressure. Index of basicity: 2 meq/g.

31 g of the compound thus obtained are heated with an equivalent weight of dipropylene glycol and 16 g of potassium acetate for 6 hours at 180° C.; after filtration of the mineral salts, the solvent is eliminated under reduced pressure.

The reactional mass is then taken up with 70 ml of absolute ethanol in the presence of 0.5 g of sodium methylate at 5.8 meq/g.

After 48 hours at ordinary temperature and neutralization of the catalyst, the solvent is eliminated under reduced pressure.

One adds to 16 g of product thus obtained (2.48 meq/g) 3.7 g of tetramer of epichlorhydrine prepared according to Example 1 (40 meq in chlorine).

The mixture is then heated at 115° C. for 70 hours.

One obtains a very thick brown paste, soluble in water.

EXAMPLE 15

The shampoo of the following composition is prepared:

| | |
|---|---|
| Compound of Example 3 | 0.5 g |
| R—CHOH—CH₂—O+CH₂—CHOH—CH₂O+₃.₅—H | 7 g |
| R represents a mixture of alkyl radicals having from 9 to 12 carbon atoms | |
| Lactic acid q.s.p. (quantity sufficient for) pH 3.5 | |
| Water q.s.p. | 100 g |

EXAMPLE 16

The shampoo of the following composition is prepared:

| | |
|---|---|
| Compound of Example 11 | 0.7 g |
| Triethanolamine lauryl sulfate | 8 g |
| Diethanolamides of coprah fatty acids | 3 g |
| Lactic acid q.s.p. pH 6.5 | |
| Water q.s.p. | 100 g |

EXAMPLE 17

The shampoo of the following composition is prepared:

| | |
|---|---|
| Compound of Example 8 | 1 g |
| R—CHOH—CH₂—O+CH₂—CHOH—CH₂O+₃.₅—H | 10 g |
| R represents a mixture of alkyl radicals having from 9 to 12 carbon atoms | |
| Diethanolamides of copra fatty acids | 4 g |
| Perfume | 0.03 g |
| Lactic acid q.s.p. pH 6 | |
| Water q.s.p. | 100 g |

EXAMPLE 18

The shampoo of the following composition is prepared:

| | |
|---|---|
| Compound of Example 14 | 0.6 g |
| Triethanolamine lauryl sulfate | 6 g |
| Lauric diethanolamide | 3 g |
| Water q.s.p. | 100 g |

Shampoos of Examples 15 to 18 clean well the hair. After cleaning the hair is soft and it can be combed out very easily.

EXAMPLE 19

The following dye composition is prepared:

| Compound of Example 8 | 1 g |
|---|---|
| N-β-amino ethyl N-methyl amino-4 phenyl azo-nitro-4'phenyl | 0.05 g |
| Water q.s.p. | 100 g |

That dye composition is applied on bleached hair during 30 minutes. The hair is, after rinsed, shampooed, rinsed again and dryed. An apricot coloration is imparted to the hair.

EXAMPLE 20

The following dye composition is prepared:

| Compound of Example 8 | 1 g |
|---|---|
| 1-N-(3-amino propyl)anthraquinone | 0.05 g |
| Water q.s.p. | 100 g |

That composition is applied on bleached hair during 30 minutes. The hair is, after rinsed, shampooed, rinsed again and dryed. An orange coloration is imparted to the hair.

EXAMPLE 21

The following dye composition is prepared:

| Compound of Example 8 | 1 g |
|---|---|
| 1,4-di-(methylamino)-2-nitro benzene | 0.03 g |
| Water q.s.p. | 100 g |

That composition is applied on bleached hair during 30 minutes. The hair is after rinsed, shampooed, rinsed again and dryed.

A nacred pink coloration is imparted to the hair.

What is claimed is:

1. Cyclical tensio-active polyethers of the general formula:

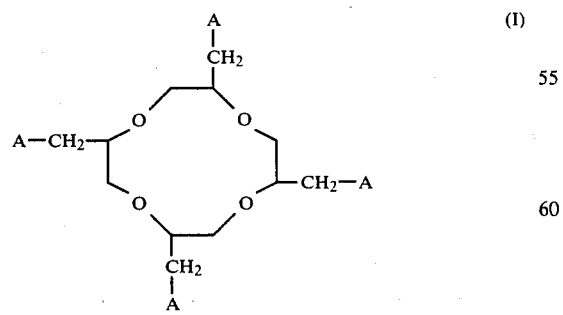

(I)

in which A is an amphiphile grouping selected from the group consisting of:

(a) the grouping:

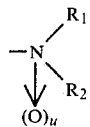

where $R_1$ and $R_2$, identical or different, refer to aliphatic radicals having from 1 to 20 carbon atoms, with one of the radicals including at least 8 carbon atoms, or substituted aliphatic radicals having from 6 to 20 carbon atoms, or alkylaryl radicals having from 6 to 20 carbon atoms, the sum of the carbon atoms of $R_1$ and $R_2$ being less than or equal to 28, or one of the radicals refers to a dimethylamino-ethyl or -propyl radical, diethylamino-ethyl or -propyl radical, piperidino -ethyl or -propyl radical, morpholino-ethyl or -propyl radical or alkyl polyhydroxy propylene radical, and u refers to the number zero or 1;

($a_1$) the grouping:

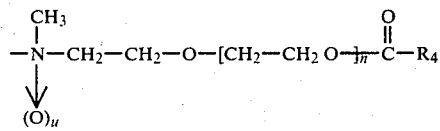

where $R_4$ refers to a non-substituted or substituted aliphatic radical or an alkylaryl radical having from 6 to 20 carbon atoms, n refers to a whole number or a fraction from 1 to 20, and u refers to a number 0 or 1;

($a_2$) the grouping:

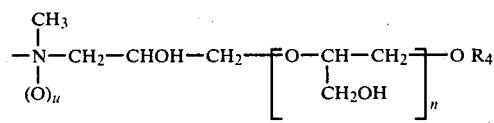

where u, $R_4$ and n having the meaning indicated above;

(b) the grouping:

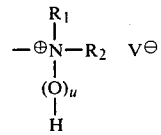

($b_1$) the grouping:

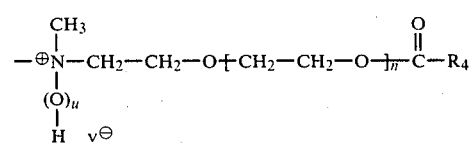

($b_2$) the grouping:

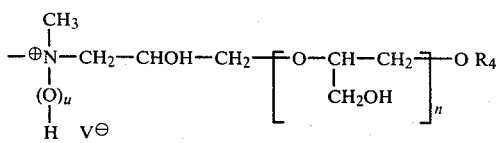

where in the groupings (b), (b$_1$), and (b$_2$) V$^\ominus$ refers to a formiate, acetate, citrate or lactate anion, and u, n, R$_1$, R$_2$ and R$_4$ have the meanings indicated for the groupings a and a$_1$;

(c) the grouping:

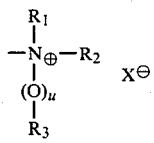

where R$_1$, R$_2$ and u having the meaning indicated for the grouping (a), R$_3$ refers to an alkyl or hydroxyalkyl radical having from 1 to 3 carbon atoms or to a benzyl radical, and X$^\ominus$ refers to a chloride, bromide, iodide, monomethyl sulphate, methyl sulphonate or p.toluene sulphonate anion;

(c$_1$) the grouping:

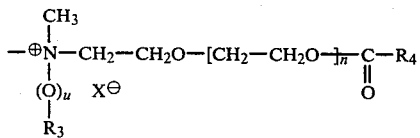

(c$_2$) the grouping:

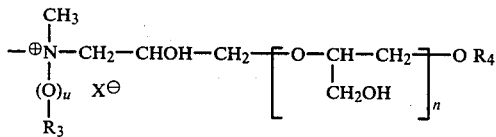

where in these groupings (c$_1$) and (c$_2$) u refers to the number 0 or 1, n refers to a whole number or a fraction from 1 to 20, and R$_4$ has the meanings indicated for the grouping (a$_1$);

(d) the grouping:

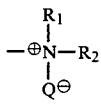

where Q$^\ominus$ refers to one of the following groupings:

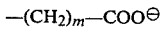

where m refers to 1, 2, or 3,

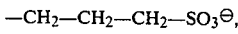

or

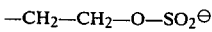

and R$_1$ and R$_2$ have the meaning indicated for the grouping (a);

(d$_1$) the grouping:

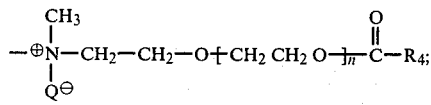

and (d$_2$) the grouping:

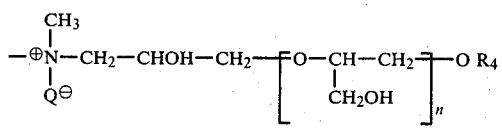

where in groupings (d$_1$) and (d$_2$) n refers to a whole number or a fraction from 1 to 20 and Q$^\ominus$ has the meaning indicated for grouping (d).

2. Cyclical tensio-active polyethers according to claim 1, wherein the amphiphile grouping A is selected from the group consisting of:

(a) the grouping:

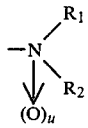

where R$_1$ and R$_2$, identical or different, refer to aliphatic radicals having from 1 to 20 carbon atoms, with one of the radicals including at least 8 carbon atoms, or substituted aliphatic radicals having from 6 to 20 carbon atoms, or alkylaryl radicals having from 6 to 20 carbon atoms, the sum of the carbon atoms of R$_1$ and R$_2$ being less than or equal to 28, or one of the radicals refers to a dimethylamino-ethyl or -propyl radical, diethylamino-ethyl or -propyl radical, piperidino-ethyl or -propyl radical, morpholino-ethyl or -propyl radical or alkyl polyhydroxy propylene radical, and u refers to the number zero or 1;

(b) the grouping:

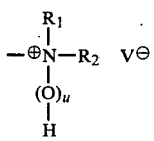

and (c) the grouping:

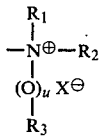

where R$_1$, R$_2$ and u having the meaning indicated for the grouping (a), R$_3$ refers to an alkyl or hydroxyalkyl radical having from 1 to 3 carbon atoms or to a benzyl radical, X$^\ominus$ refers to a chloride, bromide, iodide, monomethyl sulphate, methyl sulphonate, or p.toluene sulphonate anion, and V<sup>⊖</sup> refers to a formiate, acetate, citrate or lactate anion.

3. Cyclical tensio-active polyethers according to claim 1, wherein the amphiphile grouping A is selected from the grouping consisting of:
(a) the grouping:

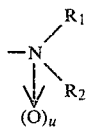

where $R_1$ and $R_2$, identical or different, refer to aliphatic radicals having from 1 to 20 carbon atoms, with one of the radicals including at least 8 carbon atoms, or substituted aliphatic radicals having from 6 to 20 carbon atoms, or alkylaryl radicals having from 6 to 20 carbon atoms, the sum of the carbon atoms of $R_1$ and $R_2$ being less than or equal to 28, or one of the radicals refers to a dimethylamino-ethyl or -propyl radical, diethylamino-ethyl or -propyl radical, piperidino-ethyl or -propyl radical, morpholino-ethyl or -propyl radical or alkyl polyhydroxy propylene radical, and u refers to the number zero or 1; and
(c) the grouping:

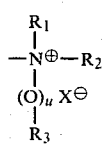

where $R_1$, $R_2$ and u have the meaning indicated for the grouping (a), $R_3$ refers to an alkyl or hydroxyalkyl radical having from 1 to 3 carbon atoms or to a benzyl radical, and $X^{\ominus}$ refers to a chloride, bromide, iodide, monomethyl sulphate, methyl sulphonate or p.toluene sulphonate anion.

4. Cyclical tensio-active polyethers according to claim 1, wherein the amphiphile grouping A is
(a) the grouping:

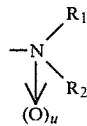

where $R_2$ and $R_2$, identical or different, refer to aliphatic radicals having from 1 to 20 carbon atoms, with one of the radicals including at least 8 carbon atoms, or substituted aliphatic radicals having from 6 to 20 carbon atoms, or alkylaryl radicals having from 6 to 20 carbon atoms, the sum of the carbon atoms of $R_1$ and $R_2$ being less than or equal to 28, or one of the radicals refers to a dimethylamino-ethyl or -propyl radical, diethylamino-ethyl or -propyl radical, piperidino-ethyl or -propyl radical, morpholino-ethyl or -propyl radical or alkyl polyhydroxy propylene radical, and u refers to the number zero or 1.

5. Cyclical tensio-active polyethers according to claim 1, wherein the amphiphile grouping A is
(b) the grouping:

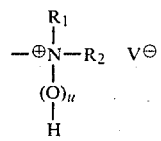

where $V^{\ominus}$ refers to a formiate, acetate, citrate or lactate anion, and u, $R_1$ and $R_2$ have the meanings indicated for grouping a.

6. Cyclical tensio-active polyethers according to claim 1, wherein the amphiphile grouping A is
(c) the grouping:

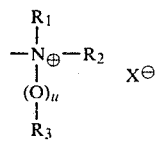

wherein $R_1$, $R_2$ and u have the meaning indicated for the grouping (a), and $R_3$ refers to an alkyl or hydroxyalkyl radical having from 1 to 3 carbon atoms or to a benzyl radical, and $X^{\ominus}$ refers to a chloride, bromide, iodide, monomethyl sulphate, methyl sulphonate or p.toluene sulphonate anion.

7. The polyethers of claim 1, wherein A is

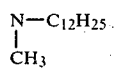

8. The polyethers of claim 1, wherein A is

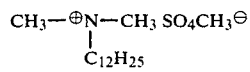

9. The polyethers of claim 1, wherein A is

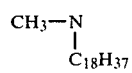

10. The polyethers of claim 1, wherein A is

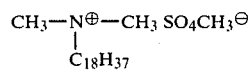

11. The polyethers of claim 1, wherein A is

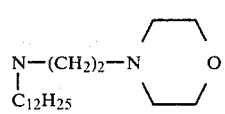

12. The compound polyethers of claim 1, wherein A is

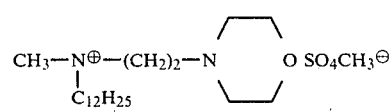

13. The compound polyethers of claim 1, wherein aliphatic refers to alkyl, hydroxyalkyl or alkenyl.

14. The polyethers of claim 1, wherein A is

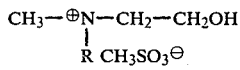

in which R is a mixture of $C_{12}$-$C_{15}$ alkyl radicals.

15. The polyethers of claim 1, wherein A is

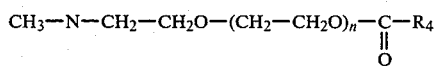

in which n has an average statistical value of 5.8 and $R_4$ is $C_{11}H_{23}$.

16. The polyethers of claim 1, wherein A is

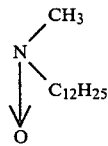

17. The polyethers of claim 1, wherein A is

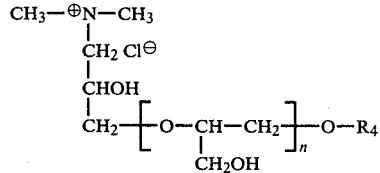

in which n has an average statistical value of 3 and $R_4$ is $C_{12}H_{25}$.

18. The polyethers of claim 1 in which $R_4$ is an alkyl, hydroxyalkyl, alkenyl or alkyl phenyl radical, the alkyl part of the alkyl phenyl radical having up to 14 carbon atoms.

19. Intermediary compound of formula (II)

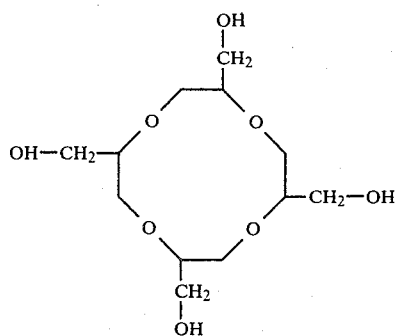

20. A cosmetic composition comprising a cosmetic carrier and at least $0.5 \times 10^{-3}$ weight percent based on the total weight of the composition of a polyether of claim 1.

21. The cosmetic composition of claim 20 in which said carrier is water or a water-alcohol solution and wherein said alcohol is an alcohol of 1-4 carbon atoms.

22. The cosmetic composition of claim 20 in the form of a cream, a gel, an emulsion or an aerosol.

23. A shampoo composition for the treatment of hair comprising a cosmetically effective quantity of at least one polyether of claim 1 in solution in a solvent selected from the group consisting of water and water-alcohol solution.

24. A cosmetic composition for the treatment of hair comprising a cosmetically effective amount of at least one polyether of claim 1 in solution in a solvent selected from the group consisting of water and water-alcohol and further containing one or more adjuvants selected from the group consisting of tensio-active anionics, cationics, amphoters, zwitterionics, non-ionics, perfumes, dyes, preservatives, thickeners, foaming agents, foam synergists, stabilizers of foam, softening agents, body agents for hair, antidandruff agents, electrolytes and cosmetic resins.

25. The composition of claim 24 in the form of a shampoo.

26. A procedure for treatment of hair comprising the application of human hair of an effective quantity of a composition including in solution in a solvent selected from the group consisting of water and water-alcohol a cosmetically effective quantity of one or more polyethers of claim 1.

27. A dye composition for the hair containing in an water or water-alcohol solution at least one polyether of claim 1 and one or more dyes selected from the group consisting of anthraquinone dyes, azoic dyes, nitrobenzene dyes, indoaniline dyes, indophenol dyes, and indamine dyes in an amount of 0.001 to 1% by weight of said dye composition.

28. A dye composition according to claim 27 also containing at least one cosmetic adjuvant selected from the group consisting of anionic, cationic, non-ionic, and amphoteric tensio-actives, perfumes, preservatives, thickeners, softeners, electrolytes, sequestering agents, penetrating agents, swelling agents and cosmetic resins.

* * * * *